United States Patent
Karch

(10) Patent No.: US 11,420,041 B2
(45) Date of Patent: *Aug. 23, 2022

(54) BLOOD PUMP CONTROL SYSTEM AND METHOD FOR CONTROLLING A BLOOD PUMP

(71) Applicant: Berlin Heart GmbH, Berlin (DE)

(72) Inventor: Dominik Karch, Berlin (DE)

(73) Assignee: Berlin Heart GmbH, Berlin (DE)

( * ) Notice: Subject to any disclaimer, the term of this patent is extended or adjusted under 35 U.S.C. 154(b) by 119 days.

This patent is subject to a terminal disclaimer.

(21) Appl. No.: 16/108,968

(22) Filed: Aug. 22, 2018

(65) Prior Publication Data

US 2018/0369468 A1 Dec. 27, 2018

Related U.S. Application Data

(63) Continuation of application No. 15/022,625, filed as application No. PCT/EP2014/070156 on Sep. 22, 2014, now Pat. No. 10,080,830.

(30) Foreign Application Priority Data

Sep. 20, 2013 (EP) ..................................... 13185363

(51) Int. Cl.
*A61M 60/00* (2021.01)
*A61M 60/892* (2021.01)
(Continued)

(52) U.S. Cl.
CPC .......... *A61M 60/892* (2021.01); *A61M 60/50* (2021.01); *G06N 3/08* (2013.01); *A61M 60/148* (2021.01); *A61M 60/205* (2021.01); *A61M 60/422* (2021.01); *A61M 60/562* (2021.01); *A61M 60/82* (2021.01);
(Continued)

(58) Field of Classification Search
CPC .... A61M 1/10; A61M 1/1001; A61M 1/1086; A61M 1/122; A61M 2205/33; A61M 2205/3331; A61M 2205/3365; G06N 3/08
See application file for complete search history.

(56) References Cited

U.S. PATENT DOCUMENTS 6,050,932 A 4/2000 Franchi
7,850,616 B1 * 12/2010 Gill .......................... A61B 7/00
600/526

(Continued)

FOREIGN PATENT DOCUMENTS

CN 1222862 A 7/1999
CN 1552282 A 12/2004
(Continued)

OTHER PUBLICATIONS

Mitchell, T. (2006). The discipline of machine learning (CMU ML-06 108). (Year: 2006).*
(Continued)

*Primary Examiner* — Allen Porter
(74) *Attorney, Agent, or Firm* — Crowell & Moring LLP

(57) ABSTRACT

Methods are provided for controlling the speed of a pump based on a valve state index and/or for deriving a valve state from time-series signal representing a pressure difference or a flow rate. The methods may be employed in blood pump systems or in blood pump control systems.

16 Claims, 8 Drawing Sheets

(51) Int. Cl.
*A61M 60/50* (2021.01)
*G06N 3/08* (2006.01)
*A61M 60/82* (2021.01)
*A61M 60/148* (2021.01)
*A61M 60/205* (2021.01)
*A61M 60/422* (2021.01)
*A61M 60/562* (2021.01)

(52) U.S. Cl.
CPC .............. *A61M 2205/3331* (2013.01); *A61M 2205/3334* (2013.01); *A61M 2205/52* (2013.01); *A61M 2230/005* (2013.01); *A61M 2230/04* (2013.01); *A61M 2230/30* (2013.01)

(56) References Cited

U.S. PATENT DOCUMENTS

| | | | |
|---|---|---|---|
| 2003/0153837 A1* | 8/2003 | McIntyre | A61B 7/04 600/485 |
| 2003/0216653 A1* | 11/2003 | Poliac | A61B 5/022 600/500 |
| 2004/0167417 A1* | 8/2004 | Schulhauser | A61B 7/003 600/513 |
| 2005/0159639 A1 | 7/2005 | Skliar et al. | |
| 2006/0094967 A1* | 5/2006 | Bennett | A61B 5/7239 600/508 |
| 2008/0249456 A1 | 10/2008 | Inamori et al. | |
| 2008/0281218 A1* | 11/2008 | Lei | A61B 6/541 600/523 |
| 2010/0022900 A1* | 1/2010 | Peterson | A61B 5/029 600/508 |
| 2010/0113945 A1* | 5/2010 | Ryan | A61B 5/053 600/486 |
| 2012/0078030 A1 | 3/2012 | Bourque | |
| 2012/0078031 A1 | 3/2012 | Burke et al. | |
| 2013/0289641 A1* | 10/2013 | Gustafsson | A61B 5/1116 607/18 |
| 2015/0141842 A1* | 5/2015 | Spanier | A61M 60/205 600/478 |

FOREIGN PATENT DOCUMENTS

| | | |
|---|---|---|
| CN | 102046077 A | 5/2011 |
| JP | 2000-504611 | 4/2000 |
| JP | 2008-264512 | 11/2008 |
| WO | WO 2010/039876 A1 | 4/2010 |

OTHER PUBLICATIONS

Te-Ming Huang, Vojislav Kecman, and Ivica Kopriva. 2006. Kernel Based Algorithms for Mining Huge Data Sets: Supervised, Semi-supervised, and Unsupervised Learning (Studies in Computational Intelligence). Springer-Verlag, Berlin, Heidelberg. (Year: 2006).*

Crisci et al. "A review of supervised machine learning algorithms and their applications to ecological data". Ecological Modelling 240 (2012) 113-122 (Year: 2012).*

Nicolas Aristokleous, Effects of Posture Change on the Geometry and Hemodynamics of the Human Carotid Bifurcation. PhD Dissertation, Lemesos, Cyprus University of Technology, 2013. (Year: 2013).*

Hu, F., & Hao, Q. (Eds.). (2013). Intelligent Sensor Networks: The Integration of Sensor Networks, Signal Processing and Machine Learning (1st ed.). CRC Press, https://doi.org/10.1201/b14300 (Year: 2013).*

Mitchell et al. "Expanding application of the Wiggers diagram to teach cardiovascular physiology". Adv Physiol Educ. Jun. 2014; 38(2): 170-175. (Year: 2014).*

International Search Report, issued in International Application No. PCT/EP2014/070156, dated Jun. 8, 2015, pp. 1-8, Rijswijk, Netherlands.

English translation of Japanese Office Action, issued in JP Application No. 2016-515531, dated Jun. 1, 2018, pp. 1-4, Japan Patent Office, Tokyo, Japan.

* cited by examiner

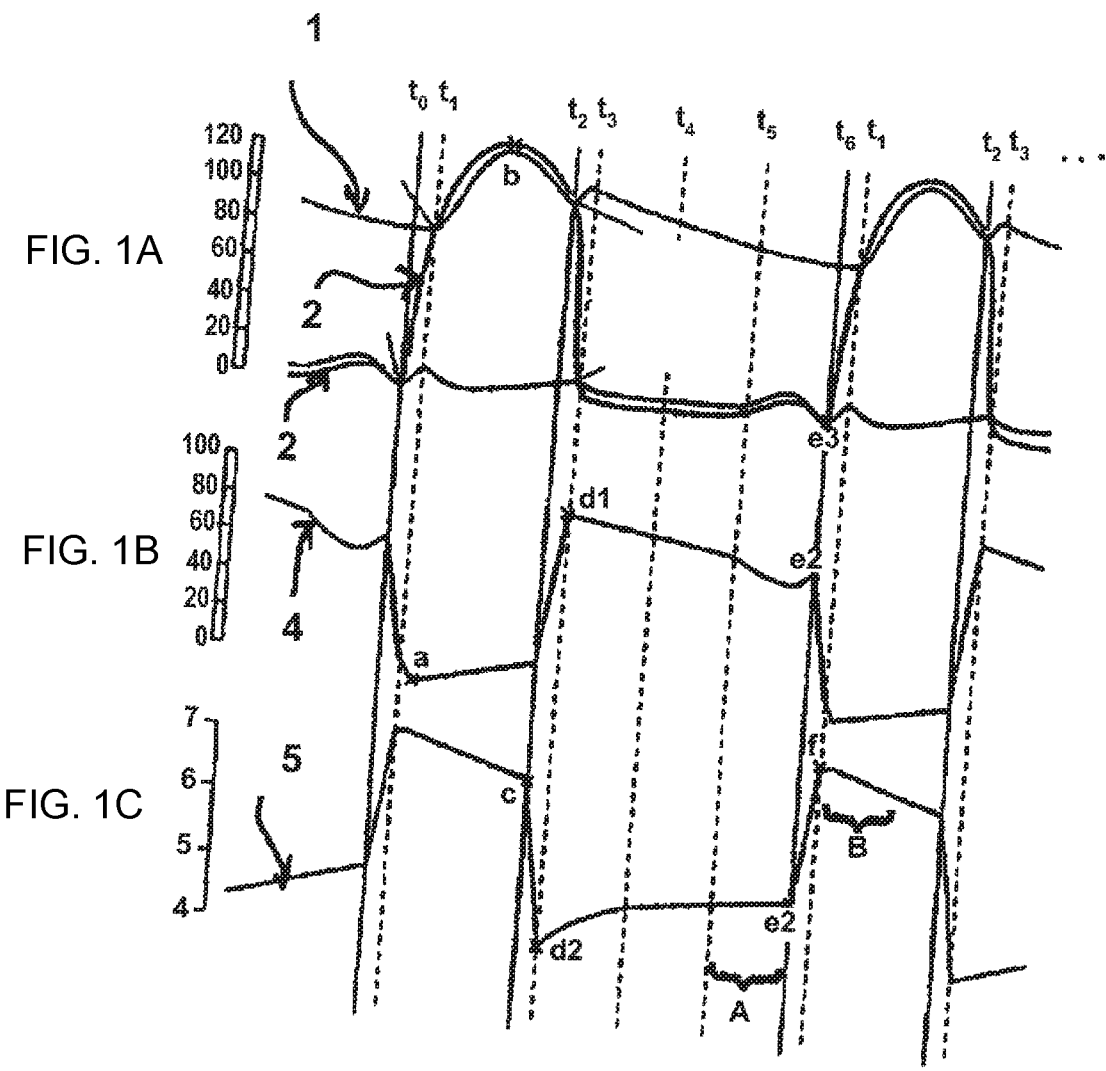

FIG. 2A
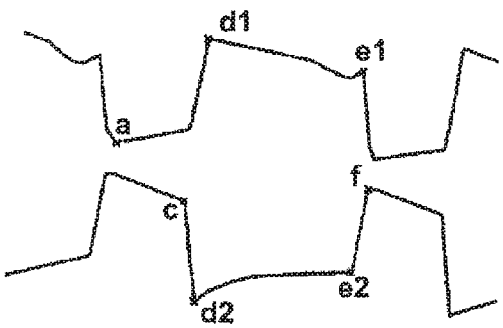
FIG. 2B
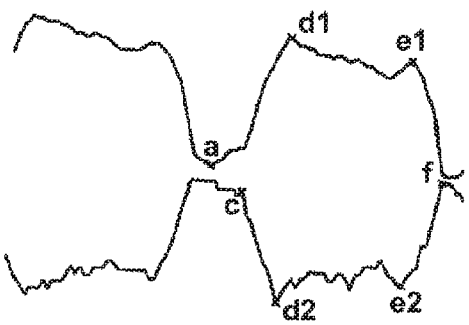
FIG. 2C
FIG. 2D
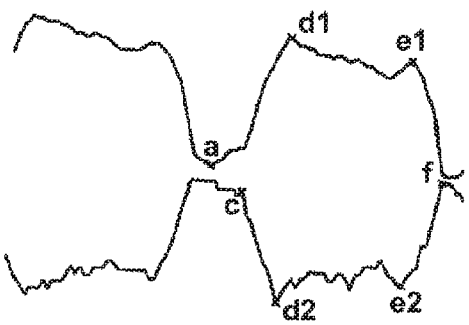
FIG. 3A
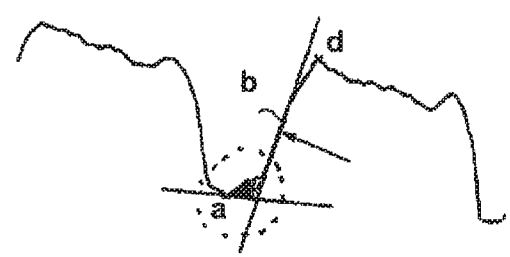
FIG. 3B
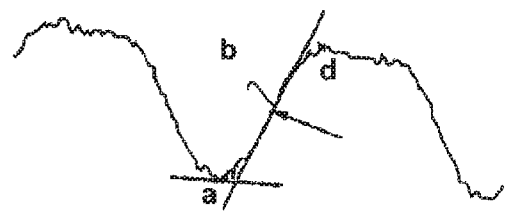

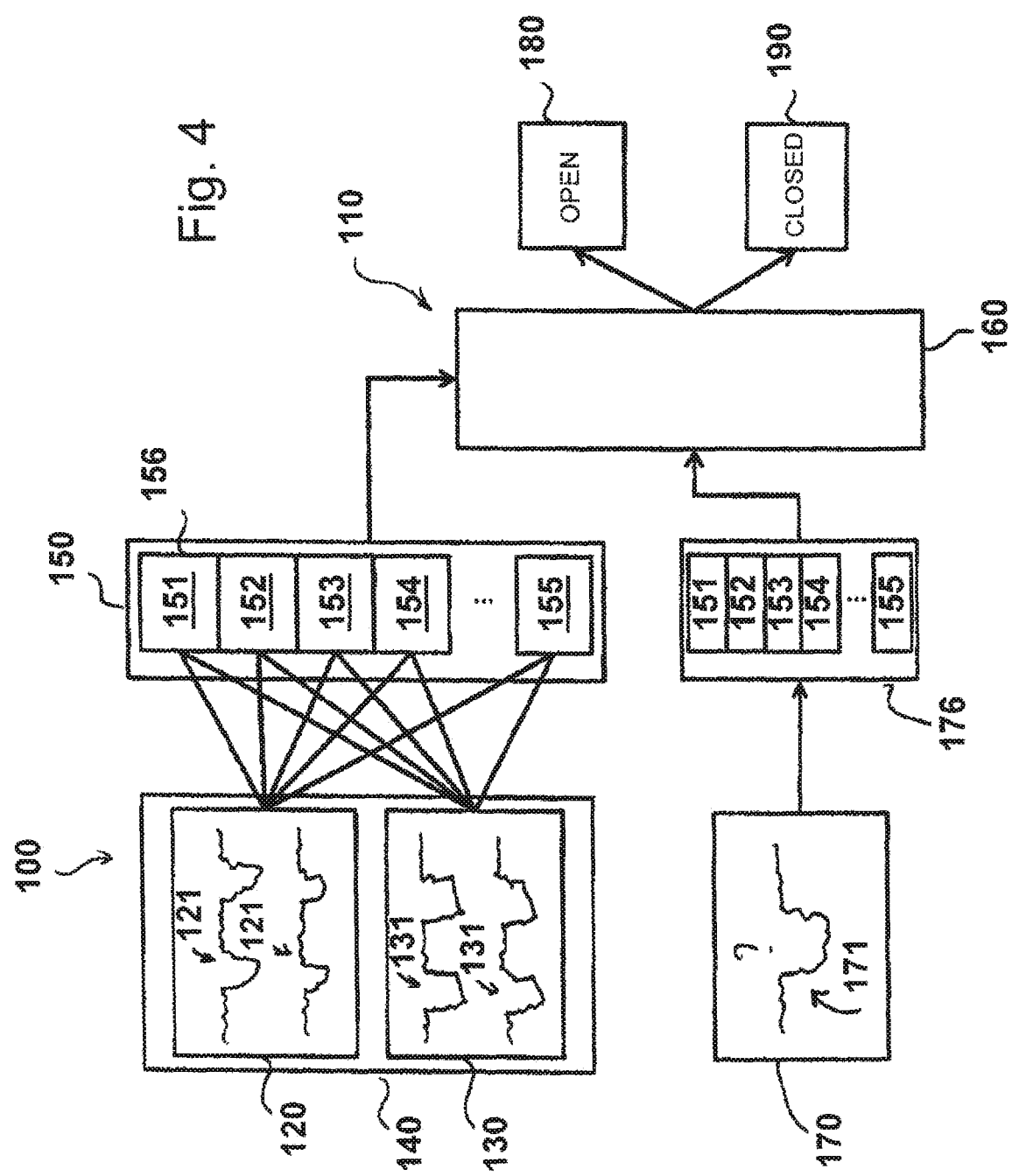

BLOOD PUMP CONTROL SYSTEM AND METHOD FOR CONTROLLING A BLOOD PUMP

CROSS-REFERENCE TO RELATED APPLICATIONS

This is a continuation of U.S. non-provisional application Ser. No. 15/022,625, filed Mar. 17, 2016, which is a 371 nationalization of PCT/EP2014/070156, entitled "BLOOD PUMP CONTROL SYSTEM AND METHOD FOR CONTROLLING A BLOOD PUMP," having an international filing date of Sep. 22, 2014, the entire contents of which are hereby incorporated by reference, which in turn claims priority under 35 USC § 119 to European patent application 13185363.2 filed on Sep. 20, 2013, entitled "Blood pump control system and method for controlling a blood pump," the entire contents of which are hereby incorporated by reference.

TECHNICAL FIELD

This document relates to blood pumps, and more particularly to blood pumps systems for controlling a blood pump, methods for controlling a speed of a blood pump, and methods for generating a signal indicative of a valve state.

BACKGROUND

Blood pumps are used to provide support for the left, the right, or both heart ventricles. These so called left ventricular assist devices (LVAD), right ventricular assist devices (RVAD) or biventricular assist devices (BVAD) can be used to maintain the mechanical functions of the heart while a patients awaits a heart transplantation, or recovers after a heart disease such as a myocardial infarction. In the following the above ventricular assist devices are abbreviated by VAD. VAD systems can be implanted, such that the discomfort for the patient is minimized. In order to determine how much blood needs to be pumped by the pump, methods for measuring the blood flow have been commercialized.

VAD systems often produce a flow which circumnavigates one of the heart's valves such as the aortic, mitral or pulmonary valve. However, it is desired that the heart valves functions are maintained. Thus, a need exists to determine whether one of the heart valves opens or closes during a heart cycle including a single systole and diastole during pump operation.

U.S. Pat. No. 6,066,086 discloses a method for controlling the speed of a blood pump wherein the speed of the blood pump is controlled by determining a valve state of each of the atrial and mitral valves by either the motor current or by using acoustic information of the heart. In order to determine whether said valves are open or closed, the document suggests an acoustic transducer to listen to heart sounds and to output a signal to a micro processor whether the valves where open or not.

US 2010/0222634 A1 discloses a blood pump wherein the state of the aortic valve is assumed to be open when a left ventricular pressure is equal to the aortic pressure or the left ventricular pressure is greater than the arterial pressure. In order to measure both pressures the blood pump includes a first sensor located at an inflow conduit and a second sensor located at an outflow conduit. The document further assumes that the blood pressure at the inflow conduit in an LVAD reflects the left ventricular pressure, while the second sensor located at the outflow conduit reflects the aortic pressure. However, the method is based on the assumption that if the left ventricular pressure was greater or equal than the arterial pressure, then the aortic valve was open. However, the state of the aortic valve cannot be reliably deduced from the ventricular and arterial pressure values only.

BRIEF DESCRIPTION OF THE DRAWINGS

FIGS. 1a-c shows an idealized Wiggers diagram over a full heartbeat cycle and corresponding pressure difference and flow rate diagrams;

FIGS. 2a-d shows a comparison of idealized pressure difference and flow rate curves and realistic time-series pressure difference and flow rate data;

FIGS. 3a-c shows exemplary signal characteristics derived from time-series data;

FIG. 4 illustrates an example of a trained classifier for classifying the valve state of a heartbeat cycle;

DETAILED DESCRIPTION

Figure 5:
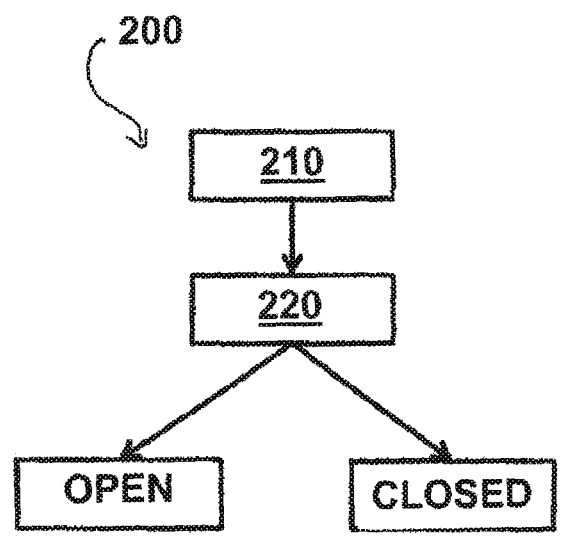
FIG. 5 illustrates a classifying scheme.

Thus, the need exists for a blood pump control system and a method for controlling a blood pump, which may determine a valve state more reliably than previous methods. In a first aspect, this document discloses a method for generating a signal indicative of a valve state.

The method includes receiving a time-series signal representing a pressure difference between a first blood pressure and a second blood pressure over at least one heartbeat cycle.

A heartbeat cycle is defined to include data of the systole and at least the beginning of the diastole. It is not necessary for the time-series signal of the heartbeat cycle to include data over various entire cycles from the beginning of the systole until the end of the diastole, even though this is the case in several embodiments of the first aspect. It is sufficient to receive data for each heartbeat cycle of the signal which includes the systole and the beginning of the diastole.

The time-series signal indicative of a pressure difference may be derived from two separate time-series signals, each signal indicative of the first or second blood pressure, respectively and each signal measured by a separate sensor. However, the time-series signal indicative of a pressure difference may also be derived from a single sensor, such as a pressure difference sensor or a signal indicative of an axial displacement of a rotating member of a blood pump.

Further examples of the signal indicative of the pressure difference can be a time-series signal derived from a bearing of the pump. One example is a voltage time-series received from a measurement coil of an axial bearing. The position of the impeller from the measurement coil can be an almost linear function with respect to an impedance change in said measurement coil; and the corresponding changes in the voltage time-series due to the impedance change have a roughly linear relation to a pressure difference between the inlet and the outlet of the pump. While in some examples a current or voltage time-series signal from a motor of an axial pump can be used in addition to a signal indicative of the pressure or pressure difference, the motor current is not suited to be the only signal used to derive a valve opening in axial pumps. In other embodiments, the time-series signal used to derive a valve state may be a pressure signal, such as the ventricular pressure.

The received signal is processed, and at least one signal characteristic is derived from the signal. A signal characteristic may be defined as a relationship between at least two data points of the signal or a value derived from at least two data points of the signal, such as a derivative of the signal. The time-series signal may be processed in the time domain and/or frequency domain. Furthermore, the time-series signal may be processed by digital or analogue methods.

In other words, the signal characteristic extracts information from the signal, which captures certain aspects related to a valve state and which reduces the number of data points used in comparison to the number of data points of the entire time-series signal.

The at least one signal characteristic is used to classify the valve state during the at least one heartbeat cycle. In the case of the aortic, mitral or pulmonary valve, the valve states are either "open" or "closed". A classifying mechanism, such as a classifier, receives the derived signal characteristic and outputs an indication whether the valve was opened or closed during the at least one heartbeat cycle.

In case of the aortic valve, the first blood pressure is the left ventricular pressure, the second blood pressure is the aortic pressure (or vice versa), in case of the pulmonary valve, the first blood pressure is the right ventricular pressure, the second blood pressure is the pulmonary artery pressure (or vice versa) and in case of the mitral valve the first blood pressure is the atrial pressure and the second blood pressure is the ventricular pressure (or vice versa).

Based on the output of the classifier a signal indicative of the valve state is generated and a pump control system may use the signal to adapt its working parameters, particularly the motor speed. The signal indicative of the valve state may also be generated by the classifying mechanism.

The method allows the generation of a signal indicative of a valve state using pump operation parameters only. Instead of needing, for example, additional acoustic transducers, a sensor system for sensing a pressure difference is sufficient. The sensor system may be embedded in the pump itself and in some embodiments all time-series signal data is received from sensors located within the pump housing, i.e. no additional sensors located outside the pump housing may be necessary, for example, external pressure sensors attached to heart or vascular tissue directly.

In a second aspect, this document discloses a method for generating a signal indicative of a valve state as in the first aspect, but the received time-series signal represents a flow through the pump between a region of a first blood pressure and a region of a second blood pressure. Correspondingly, the at least one signal characteristic is derived from the time-series signal representing the flow. While the method according to the second aspect utilizes a flow sensor, the method of the first aspect relies on the pressure difference. It appears that classifying mechanisms using data from the method of the first aspect have an improved success rate in classifying the signal correctly.

In one embodiment of the first and second aspects, the at least one derived signal characteristic is based on the waveform of the time-series signal. The inventors have found that the shape of the waveform of a signal indicative of a pressure difference or a signal indicative of the flow during the systole and at least the beginning of the diastole has several signal characteristics which are different for an open and a closed valve state. The waveform may contain asymmetries which can be exploited to extract signal characteristics.

In a further embodiment, the at least one signal characteristic may be based on one of the following characteristics. In the following, several examples of signal characteristics are given for an aortic valve. However, a person of ordinary skill in the art will understood how these specific signal characteristics are adapted to reflect openings of the mitral or pulmonary valves.

In a first example, a difference, PULS, of a minimal, MIN, and a maximal, MAX, signal value over a heartbeat cycle may be used, the signal being indicative of a pressure difference or a flow. It appears that the difference includes information whether a valve had opened during the cycle or not. A further example of a signal characteristic is a (positive) extremal value, EXT_V, of a derivative of a signal value between the minimal and the maximal value of a signal indicative of a pressure difference or between a maximal and a minimal value of a signal indicative of a flow (negative extremal value). The extremal value, i.e. the highest or lowest value can be used to distinguish between heartbeat cycles with a valve opening and without a valve opening. A further example is a quotient, RELPULS corresponding to PULS over MAX_N, where MAX_N is proportional to the maximal signal value within a predetermined number of preceding heartbeat cycles including of heartbeat cycles preceding including the first heartbeat cycle. Another example is the time interval, DUR, between a minimal value and an intersection point of two tangent lines, the first tangent line being a horizontal line through the data point corresponding to the minimal value and the second tangent line running through the data point of the signal, at which the derivative has an extremal value (see above). A further example is an angle, ANGLE, between the tangent line through an extremal point and a line through the time-series values at the beginning and a value of the time-series signal corresponding to an end value of the interval DUR. A further example is the area, AREA, between the two tangent lines and the signal values. These signal characteristics on their own, in combination or in combination with further signal characteristics may be used to classify the valve state of the at least one heartbeat cycle reliably. In a further embodiment, the chosen signal characteristic is AREA and optionally at least one further signal characteristic.

The above examples do compare values of data points of the signal to other data points of the signal, thereby reducing the effects of trending which are frequently found in human physiologic data and which often affect the data values, but not the content found within the data. This improves the reliability of the classifier. However, other signal characteristics, such as the sign of the value of the data points can supplement the previous values derived from a comparison of values of different data points within one or several heartbeat cycles.

Consequently, when more than one signal characteristic is derived from the time-series signal, the classification may be based on more than one signal characteristic.

In a further embodiment, the time-series signal over at least one heartbeat cycle is analyzed and, if necessary, is separated into signal fragments, i.e. subsets of signals, where each signal fragment or signal of a subset includes data from one heartbeat cycle only. Additional data may be discarded in some embodiments. The separation may positively affect the quality of the results of the classification process. Furthermore, when extracting signal characteristics, it might be beneficial to pre-analyse the signals by separating the signal into signals including a single heartbeat only or to separate signal segments and to detect the points of interest before forwarding the signal characteristics to a classifier, to improve the quality of the results, tests can be conducted to test whether the signal segments or the detected point of interest have been detected and segmented correctly. Such tests can be based on separated classifying system.

As will be discussed later within this document, the signal characteristics may be derived from heartbeat cycles of which the valve state is known. The trained classifier may then classify based on one or more of the selected signal characteristics.

In a third aspect, this document discloses a method for training a classifier for classifying a time-series signal regarding a valve state, each signal indicative of a pressure difference or a flow or at least one signal characteristic derived from said signals.

To train the classifier, a first group of time-series signals, each signal representing data of at least one heartbeat cycle when a valve state was open, and a second group of time-series signals representing data of heart, each signal representing data of at least one heartbeat cycle when a valve state was closed, are generated.

The signals of the first and second groups may be recorded from patients suffering from conditions similar to the conditions of patients having an implanted VAD device. The signals are further analyzed and classified by a physician as open or closed. Alternatively, the signals of the first and second groups may be recorded from patients having an implanted VAD device and to simultaneously record the heart sounds by an acoustic transducer. Heart sounds allow a reliable classification whether a valve, such as the aortic, pulmonary or mitral valve was open or closed. In a further embodiment, the signals of the first and second groups may be recorded while simultaneously using ultrasound imaging to determine whether the valve state was open or not. The ultrasound recordings are used to identify whether a heartbeat cycle belongs to the first and second group. Matching the time-series signals and the corresponding heart sounds allows a very reliable classification of the signals.

After the time-series signals have been labelled as "open", "closed" or "unknown", in case no reliable conclusion can be made, at least one signal characteristic is derived from each of the signals of the first and second groups.

The at least one signal characteristic is then used to train a classifier to discriminate the valve states between, for example, "open" or "closed". Additional states, such as "probably open" or "probably closed" or "unknown" may also be considered.

For example, several classifiers described in the prior art can be chosen. As examples, the classifier to be trained may be a neural network, a support vector machine, a Gaussian classifier, a Naïve Bayes classifier, a decision tree classifier or a k-nearest neighbour classifier. Various other classifiers types, such as other linear classifiers or non-linear classifiers may also be used.

After the classifier has been trained as described above, the classifier may be used in one of the methods of the first or second aspect as a classifying mechanism. The trained classifier may be implemented as a set of machine-executable instructions such as software, firmware or hardware or electronic circuitry. The methods of the first and second aspects may also be implemented as computer-executable software, firmware or hardware or electronic circuitry or a combination thereof.

Furthermore, the methods may be implemented in a blood pump, a system including a blood pump or a blood pump controller as electronic circuitry, computer hardware, firmware or software, or a combination thereof. These encompass processor-executable programs, processor-readable set of instructions and the like.

In a fourth aspect, this document discloses a blood pump control system including means for receiving a time-series signals indicative of a pressure difference. These means can include signal detection circuitry located in the pump or a control system for the pump or a signal data bus between a pump and a control system for the pump.

The system further includes a signal characterizing circuit for deriving at least one signal characteristic from the time-series signal. This circuit may include a microcontroller or a processor configured for analyzing the signal, optionally dividing the signal in subsets of signals, for example so that each signal of a subset only includes a single heartbeat cycle, and deriving at least one signal characteristic from the time-series signal or the signals of the subset.

The at least one derived signal characteristic (which may represent only a small amount of data compared to the data of the entire time-series signal or of each signal of the subset) is input into a classifying circuit, which may include separate components or components also used in the signal characterizing circuit. The classifying circuit includes a classifying routine such as the described trained classifier, for example, to classify the signal or each of the signals of the subset to correspond to a heartbeat cycle with an open valve or a closed valve. In this sense "closed" can be understood as "not open" but can include several states such as "probably closed" or "unknown". The classifying mechanism analyzes the at least one signal characteristic and outputs a signal indicative of the valve state. This signal can include the updating of a counter, the updating of a counter during a running time window, or can apply a label to each time-series signal, the signal corresponding to the respective valve state.

However, the output signal of the classifying may also be used by a further circuit to generate a signal indicative of the valve state based on the output signal.

In one embodiment, the signal indicative of a valve state is used to construct a valve state index, VSI, which may, for example, be a valve opening index, VOI, relating the number of occurrences of an open valve state in the classified signals to the number of classified signals or a valve closing index, VCI, relating the number of occurrences of a closed valve state in the classified signals to the number of the classified signals. The VSI may be used as a part of a control loop to adjust the speed of a movable member of a pump, for example, a rotor, a piston or a membrane.

The VSI can be kept in a memory and may be updated by further signals indicative of a valve state. The VSI may be constructed by calculating the VSI from available signals indicative of a valve state. For example, a plurality of signals indicative of a valve state may be stored in memory and values stemming from older signals may be deleted for values from newer signals to have an indication of an actual VSI, reflecting the index over a predetermined number of previous heartbeat cycles or a predetermined length of time.

The actual VSI may be compared to a target VSI and the speed of the pump may be adjusted based on the comparison of the actual and target VSI values. For example, in case the VSI is a VOI, a reduction in speed may be necessary if the VOI indicates that the valve does not open a sufficient number of times over a predetermined number of heartbeat cycles to result in a desired therapeutic effect of the pump operation. In case of a VCI, the reduction may take place if the valve is closed too many times.

Whether a VOI or a VCI is used may depend on the choice of the medical practitioner or a desired therapeutic effect. For example, the chosen classifier may have an effect on the sensitivity or specificity for correctly classifying open or closed valve states. Depending on whether a high specificity or sensitivity is desirable a VOI or VCI may be chosen.

A further aspect of the application is a method for controlling a speed of a pump by constructing a valve state index, VSI, of a valve from a plurality of signals indicative of a valve state of the valve and adapting the speed of the pump based on the VSI. Preferably the signals indicative of a valve state are time-series signals, which are analyzed by a method or system as described above.

Many pumps can use a pulsatility index, PI, for the operation of a pump. However, the PI is often based on measurements of pressure, motor current, pressure differences or the like and, in this sense, do not directly correspond to a physiological phenomenon. Furthermore, the constructing of a VSI can be performed on heartbeat cycle time-series data and the additional knowledge which valve state occurred for a number of the heartbeat cycles. The pump operation is thereby adapted to each patient individually.

Using a valve state index has the benefit of relating the pump operation to the physiologic effect of the valve opening and closing. An index is in one embodiment understood as a quotient of a first number of heartbeat cycles and a second number of heartbeat cycles out of the first number of heartbeat cycles, the second number representing the number of occurrences of a chosen valve state, e.g. an open or closed valve state. An index defined as above represents a percentage of the chosen valve state occurring compared to all valve states occurring.

In a further embodiment, the VSI may be updated on the fly, i.e. using valve state indications which were determined after an initial or first construction of the VSI. For example, the oldest valve state indications may be dropped for newly determined valve state indication thereby representing an actual or current VSI based on date from a predetermined time interval only or from a predetermined number of valve state indications only.

The updating can, for example, be performed for every new valve state indication, for every fifth, tenth or hundredth valve state indication, for every new occurrence of a chosen valve state indication or, for every fifth, tenth or hundredth chosen valve state indication, or for a predetermined time interval, such as updating the VSI by using valve state indications recorded during a past second, minute or 10 minutes, for example, using the new data in addition to previous data from a minute, five minutes, ten minutes or one hour prior to the new valve state indication data. The regular updating reflects the current VSI but smoothes the occasional, irregular behavior, such as an unexpected period of the chosen valve state not occurring, even though it would be expected under normal circumstances.

In a further embodiment a predetermined total number of valve state indications from heartbeat cycle time-series data is used, such as 50, 100, 200, 350, 1000 or more are used to determine the valve state index. This can reduce the amount of data that needs to be stored for calculating and constructing the index.

In a further embodiment, the VSI may be used as a part of a closed-loop control system. After determining the current VSI, the speed of the pump may be adapted to increase or decrease the VSI to a desired target VSI. For example, if the chosen valve state is an open valve state of the aortic valve, i.e. the VSI is a valve opening index, VOI, then a low VOI may indicate that the pump transports too much blood for the valve having to open. Consequently, in some therapeutic programs, the speed of the pump would be reduced to increase the VOI to a target VOI representing valve activity due to a reduced pumping speed.

In a further embodiment, additional valve state indications are derived based on measurements of a pressure, or pressure difference, or a flow through the pump after the speed has been adapted to check whether the current VSI is closer to the target VSI. In some embodiments, the predetermined time interval or predetermined number of heartbeat cycles may be changed from an initial, larger number to a smaller number (or vice versa) depending on how far the current VSI is away from the target VSI. For larger required or desired changes of the current VSI to a target VSI, a smaller time interval or a smaller number of valve state indications may be desired, since the VSI then reflects more current events.

Furthermore, in some embodiments, the target VSI is not a single numerical value, but an interval. This has the benefit of the system being allowed to operate within a range of target VSIs, thus, reducing the need to constantly adapt the speed of the pump in a closed-loop control. The interval may be chosen as an open or a closed interval. E.g. the interval may have a range of less than 0.1 or less than 0.05 of an index running between 0 and 1.

A further aspect of this application is a system for a control of a blood pump, including a control unit including means for receiving a signal indicative of a valve state of a blood system valve. The means may be an analogue or digital signal processing circuit, for example. The system further includes a signal processing circuit configured for calculating a VSI based on the received signals. The signal processing circuit may be the same as the means for receiving the signal indicative of the valve state. Furthermore, the control unit is operably connected (via cable or wirelessly) to a motor controller connected to a motor of a blood pump, the speed of which may be adjusted based on the VSI.

In case the pump system also includes means for measuring a signal, such as a pressure difference, from which the control unit or a further unit may derive a signal indicative of a valve state, then the control system may be designed as a closed-loop control system.

In a further embodiment, the system may also include the blood pump including a motor, an inflow and an outflow conduit and a movable element for producing a flow between the inflow and outflow conduit, such as a rotor, a piston or a movable membrane.

In a further embodiment, the system may also include a comparator circuit configured for comparing a current VSI to a target VSI; and a signal processing circuit for receiving a comparator signal and sending a signal to the motor controller to adjust the speed based on the comparator signal. This comparator circuit is helpful for an automated closed-loop system.

Further aspects or embodiments can be derived from the claims or the following description of specific embodiments shown in the figures. It is noted that the specific embodiments show more elements than are necessary for the operation of the methods or the systems described by the invention. Consequently, elements shown in the Figures or described in the accompanying description may be claimed on their own at a later stage in the proceedings. Additionally, element(s) shown in one specific embodiment may be combined with element(s) shown in a different embodiment.

In a further aspect, a blood pump comprises a hollow body, in which an impeller with a blading is provided, for the production of an axial propulsion of the blood along the impeller, as well as at least partly actively stabilised axial magnetic bearing device and preferably, but not necessarily a hydrodynamic bearing device for the impeller, wherein the impeller may be set into a rotation about a rotation axis of the impeller, with a motor stator preferably but not necessarily located outside the hollow body, and wherein the hollow body comprises an inlet for the flow of blood into the hollow body in an inflow direction essentially parallel to the rotation axis, and an outlet for the flow of the blood out of the hollow body in a flow-out direction. Preferably, but not necessarily, the outlet is arranged offset with respect to the rotation axis of the impeller for producing an outflow angle between the inflow direction and the outflow direction, which is different from zero.

According to an embodiment, on the upstream-side and on the downstream-side of the impeller permanent magnet arrangements are provided and the pump has at least one actuator ring coil for actively stabilising the impeller in axial direction. In some embodiments, there is only one actuator coil.

The single actuator ring has several embodiments which make sure that the impeller is always stabilised in the axial direction.

According to a first embodiment, the only (one) actuator ring coil acts on both, the upstream-side and the downstream-side permanent magnet arrangements by using an iron yoke for transferring the magnetic flux to at least one of the permanent magnet arrangements, wherein the actuator ring coil acts directly on the remaining magnet arrangement.

In a second embodiment, the at least one actuator coil acts on only a first of the upstream-side or downstream-side permanent magnet arrangements and the other permanent magnet arrangement is configured as a passive axial bearing. Possibly, but not necessarily, this passive axial bearing arrangement comprises two magnets which attract each other and act as a 'spring' in order to pull the impeller in the desired direction. In this case, the thrust caused by the magnetic flux of the single actuator acts against the force of the spring.

In any of these axial stabilising arrangements, only one or, alternatively, both of the upstream-side and downstream-side permanent magnet arrangements of the impeller comprise a sensor system for detecting a possible deviation of the impeller from a desired axial position. In an embodiment, the at least one sensor system interacts with the actuator ring coil for correcting a possible deviation of the impeller from the desired axial position.

As will be described in further detail below, an inner radius of the hollow body is enlarged for forming a discharge channel which runs tangentially around the impeller and runs out into the outlet, for a flowing-away of the blood out of the hollow body, running essentially tangentially to the impeller. Preferably, but not necessarily, the centre of the discharge channel offsets away from the impeller in a direction axially to the rotation axis of the impeller. Thus, the discharge channel has similarities with a 'snail shell' as it preferably not only continuously widens its cross section, but has a (preferably continuously growing) offset in the direction of the rotation axis of the impeller.

In some embodiments, the impeller includes a support ring, which forms an annular gap (or several annular gaps) between the support ring and an inner wall of the hollow body. Such a support ring, preferably formed as a rotationally-symmetrical hollow cylinder, may be designed in different widths and may be fastened on the impeller at any location, in order to achieve an optimal stabilisation of the impeller, in particular with respect to tilting of the impeller. In this manner, one may compensate imbalances of the impeller in a particularly effective manner. this case, a suitable support ring directly upstream of the discharge channel in the flow direction, may contribute to a stabilisation of the impeller.

The pump may comprise a blood pump control system as described throughout this application or may incorporate a method of adapting the speed of the pump as included herein.

FIG. 1 shows a Wiggers diagram in the top panel and corresponding, idealized diagrams of a pressure difference between an aortic pressure and a left ventricular pressure (middle panel) and a diagram of a flow rate through the ventricle (bottom panel) during a heartbeat cycle over time. All pressures are shown in the unit of mmHg and the flow rate is shown in the unit of ml. The curves are representative of a human heart.

The top panel shows an idealized pressure curve of the aortic pressure 1, the left ventricular pressure 2 and the left atrial pressure 3. At time t0, the mitral valve closes and causes an isovolumic contraction up to time t1, at which the aortic valve opens. Subsequently, the left ventricle starts ejecting blood into the aorta until the aortic valve closes at time t2. The time between the closing of the mitral vale and the closing of the aortic valve is the systole. The left ventricle relaxes isovolumetrically until time t3, at which the mitral valve opens again, causing a rapid inflow of blood into the left ventricle. The rapid inflow slows down during the diastole starting at t4. With the atrial systole starting at t5, the filling of the ventricle terminates at t6, at which the mitral valve opens again, ending the heartbeat cycle.

The middle and bottom panels show the pressure difference 4 and the flow rate 5 during the heartbeat cycle. Shortly, after the opening of the aortic valve the pressure difference reaches a pressure difference minimum a. From the minimum, the pressure difference rises slowly until the closing of the aortic valve at time t2. After time t2, the pressure difference rises rapidly to a maximum dl at time t3. The pressure difference thereafter drops slightly until the eventual closing of the mitral valve again.

The corresponding flow rate 5 looks almost like a mirrored curve of the pressure difference. The flow rate rises slightly until the opening of the mitral valve and then rises rapidly until the opening of the aortic valve.

The flow then remains high and slightly drops before dropping rapidly after the closing of the aortic valve until the opening of the mitral valve.

In FIGS. 2a and b, the pressure difference 4 and the flow rate 5 are shown again. However, FIG. 2c and FIG. 2d show a more realistic time-series data of the pressure difference and the flow rate, respectively. It is easily understood that the idealized curves are merely illustrative. However, certain points of interest can be detected in the realistic time-series data, such as the minimum or maximum of the data values of the time-series.

In FIG. 3a an example of a time-series signal of a pressure difference with an opening aortic heart valve is shown, where the time-series shown in FIG. 3b is representative of a heartbeat cycle in which the aortic valve stays closed. The two time-series shown in FIGS. 3a and 3b do include noise or sampling effects. The difference is particularly evident during the ventricular systole and the isovolumetric relaxation of the ventricle. The inventors have found that while the maximal and minimal values may vary between heartbeat cycles with an opening aortic valve and a closed aortic valve, the PULS of heartbeat cycles with a closed aortic valve vary not too much between different heartbeat cycles with a closed cycle and they are comparatively smaller than the PULS of heartbeat cycles with an open aortic valve. These effects are better visible when looking at the pressure difference, in contrast to the minimal or maximal values of the pressure time-series, which are not well suited to construct a reliable classifying scheme to determine whether the aortic valve was open or closed during a particular heartbeat cycle.

Looking at the pressure difference time-series improves the reliability for correctly determining the valve state, e.g. open or close. However, while the absolute values of points of interests, such as the minimal or maximal values of the pressure difference (or flow rate) have a positive effect on the reliability, looking at at least one different signal characteristic may greatly improve the reliability of the classifying step or the classification overall.

Figure 3C:
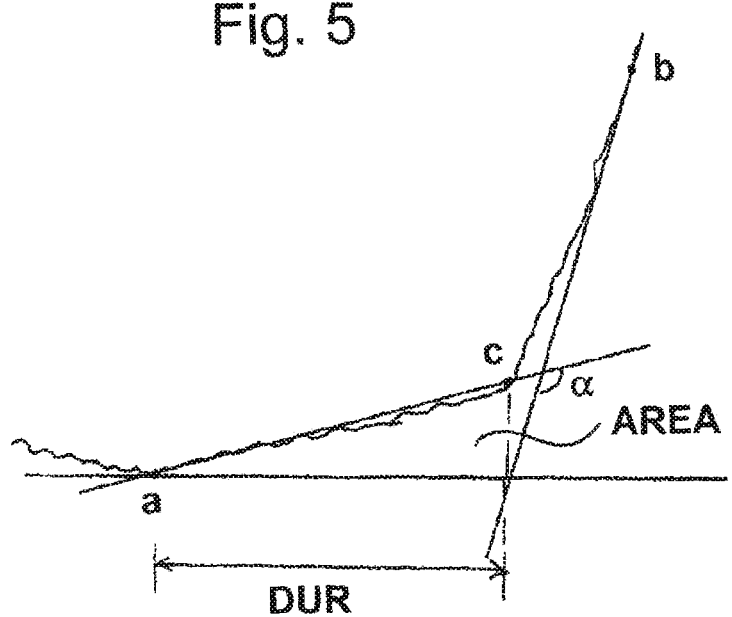

FIGS. 3a and 3c, besides the time-series data, indicate the minimum values a, the maximal values d, as well as tangent line through minimum a (i.e. a horizontal line) and a tangent line through an extremal value data point b between values a and d, i.e. a tangent through the value of the extremum of the derivative of the time-series. Furthermore, the area which is bordered by the two tangent lines and the time-series is depicted as a filled area.

In the chosen data samples it is easy to see that the AREA of an open valve and of a closed valve state are significantly different from each other (among others). Hence, by deriving signal characteristics from the curve that go beyond the absolute values of the time-series (i.e. higher-order signal characteristics), it becomes easier to identify differences between heartbeat cycles with an opening aortic valve and heartbeat cycles with a closed valve.

FIG. 3c shows the time-series values, the minimal value a, the horizontal line and the tangent line running through extremal value b, the area, AREA, bordered by the tangent lines and the time-series, an angle α, ANGLE, between the tangent line running through extremal value b and a line through the time-series values at the beginning, i.e. through point a and a value c of the time-series signal corresponding to the end of the interval DUR. While these are some examples of higher-order signal characteristics, other examples may be envisioned. For example, corresponding data characteristics may be derived between a maximal value before or right after the start of the ventricular systole and the minimal value a.

It has been found that AREA for heartbeat cycles including an aortic valve opening is, on average, larger than the corresponding area of a heartbeat cycle with a closed aortic valve. Furthermore, the time interval between the time of the minimal value a and the intersection point of the two tangent lines is, on average, larger for heartbeat cycles with an opening aortic valve than for a heartbeat cycle with a closed aortic valve.

Further examples of higher-order signal characteristics are a difference between a minimal value a and a maximal value d. As a further example of a signal characteristic involving more than one heartbeat cycle, a difference between a minimal value of a current heartbeat cycle and the maximum of the maximal value d of a number of past heartbeat cycles may be derived. The number may be predetermined or random. The number can be, for example, between 2 and 10. The signal characteristics may be normalized to their respective heartbeats, e.g. the numerical values obtained from the signal characteristics can be divided by the length of the heartbeat cycle. This may be an improvement when comparing different data to derive the valve state of a heartbeat cycle.

While a single signal characteristic may improve reliability of determining a valve state, analyzing several signal characteristics and using these signal characteristics during classification of online data may further improve the reliability.

The time-series data is pre-processed and in some embodiments sampled and/or separated in sets of subsignals, each subset comprising only one full heartbeat cycle. However, the derivation of signal characteristics can also be performed on time-series including more than a single heartbeat cycle.

Thereafter, a signal processing circuit or signal processing software determines particular data points, for example minimal, maximal and extremal values, by known signal analysis routines. From the determined values the signal characteristics are constructed and used for classifying the heartbeat cycle from which the signal characteristics were extracted. Thus, the time-series data of the pressure difference signal of a heartbeat cycle, which may be large, is collapsed to a small set of data points describing the signal characteristics to be used for classifying and in some embodiments a time stamp or a identification number. The small set of data points including the one or more signal characteristic and a time stamp or identification number can be used to determine the valve state for each heartbeat cycle. The determined valve state (i.e. signal indicative of the valve state can be used to control the pump operation by maintaining, increasing or reducing the speed of the pump depending on the target range of a valve state index, i.e. depending on whether the current valve state index is equal, below or above the desired target range.

In the above embodiment, the time-series data of the pressure difference or flow rate is reduced to a vector representing signal characteristics and higher-order signal characteristics of the time-series, in some embodiments keeping a single vector per determined heartbeat only. This vector may then be further reduced to a single value indicating whether the valve state was opened or closed when the vector is entered into the chosen or trained classifier. However, it is also possible to derive a vector of signal characteristics and derive the valve state from said vector directly instead of saving the vector and deriving the valve state by feeding the vector to the classifier at a later point in time. While some embodiments may keep timing information, other embodiments may not keep timing information, but only information whether the valve was open or closed for a specific heartbeat. The exact opening or closing times of the valve may not be necessary in those embodiments.

Even though, in the embodiments discussed so far only one type of time-series signals is analyzed and signal characteristics are extracted from this one type of signal. However, signal characteristics can also be extracted from more than one time-series signals types. By means of using signal characteristics of more than one type of signal the overall accuracy of the classification may be improved.

It is noted that the partitioning of heart time-series data into subsets of data containing a single heartbeat cycle only are well known in the art, e.g., the local minimum of the pressure difference curve can be detected. Alternatively, methods known from the signal processing of electrocardiograms can be used. Furthermore, the methods, systems and apparatuses discussed in this document may include methods for sampling and preprocessing time-series data, such that the time-series data can be analyzed and a valve state may be determined.

FIG. 4 shows a schematic overview of how a classifier can be trained and how a trained classifier can be used to derive a valve state from actual time-series data to be analyzed, e.g. live online or stored time-series data.

FIG. 4 illustrates an embodiment of a method of training a classifier which may be used for classifying heartbeat time-series data.

The method 100 of training a classifier 110 includes the selection of signal characteristics from at least one type of time-series signals representing data recorded over one or more heartbeat cycles.

In the present embodiment, the classifier includes 5 signal characteristics including the difference between a maximal and a minimal value of time-series data of a pressure difference between the left ventricle and the aorta. This signal is well suited for training a classifier to classify whether the state of the aortic valve during a heartbeat cycle was open or closed. However, different signals can be chosen such as a pressure difference between the right ventricle and the pulmonary artery which is well suited to classify the state of the pulmonary valve or a pressure difference between an atrium and the corresponding ventricle which is well-suited to classify the state of the mitral valve connecting the atrium and the ventricle. Furthermore, the signal could in some embodiments also be a flow rate through a pump. In other embodiments a ventricular pressure may be used as the signal to derive the valve state during a heart beat. This may be the case, if the signal shows similar higher order signal characteristics as the signal indicative of the pressure difference and if those higher order signal characteristics (or any one of the signal characteristics) correlate with the valve state.

In the present example, the time-series data has already been divided into subsections which contain data from a single heartbeat cycle only. In FIG. 4 the data set of time-series data of heartbeat cycles during which the aortic valve was closed is denoted by reference sign 120, the data set of time-series of heartbeat cycles during which the aortic valve opened is denoted by reference sign 130. Both data sets 120 and 130 contain several subsections 121 and 131, respectively. The division into several subsections may be performed by a signal preprocessing circuit or algorithm 140. The preprocessing of the subsections or the time-series data in general may further include standard procedures such as high, low or band-pass filtering, sampling of analogue recorded data and the like. A plurality of subsections 121 and 131, respectively is processed by a signal characterizing circuit or by a signal characterizing algorithm 150, which derives at least one signal characteristic 151 from the subsection to be analyzed. Further signal characteristics 152 through 155 may be derived by the same circuit or algorithm or, in other embodiments, by additional circuits or algorithms. For each of the plurality of subsections the one or more signal characteristics 151 through 155 are derived. In the embodiment described by FIG. 4, the signal characteristics 151 through 155 are grouped as a vector 156. This vector 156 is used to train the classifier 110, however, the classifier may also be trained by additional vectors and/or by not using each and every entry of a vector. The classifier is a Naïve-Bayes classifier and is trained to recognize a difference between the data sets 120 and 130, so that real data can be classified reliably by the trained classifier. Since it is assumed to be known for each subsection whether the subsection include a valve opening or nor, it is possible to train the classifier to correctly classify data for which the valve state is not known. From the theory and mathematical or experience background of the chosen classifier it can be estimated how many subsections are necessary from each data set to obtain a trained classifier having a desired confidence interval of the specificity and sensitivity or reliability. The reliability criterion may be formulated to correctly classify the real data in more than 70% or more of all cases. The specificity and sensitivity criteria take into account that some applications of the classifier may use said classifier to be sure that the presented data was of a heartbeat cycle with an open or closed valve, respectively, i.e. reducing the number of false positives or specificity. The same applies to the sensitivity which aims at reducing the number of false negatives. However, when applying these criteria it has to be decided whether the open or closed state is a positive or negative in order to determine a false positive or negative.

The classifier 110 is a hard-wired, software or firmware-based algorithm which is trained by using time-series data from signals including heartbeat cycles for which the valve state (in this case the aortic valve) is known. The trained classifier may be uploaded into a signal classifying circuit or algorithm 160 and then be used to classify real data.

This is further illustrated by the application of the trained classifier to real time-series data 170 of a signal type corresponding to the signal type(s) used in data sets 120 and 130 which has been preprocessed into subsections. For each subsection 171, one or more signal characteristics 151 through 155 may be derived or extracted. These signal characteristics need to include the signal characteristics which were used to train the classifier 110. The trained classifier 110 reads the vector 176 and classifies it as representing a heartbeat cycle including a valve opening, OPEN (180) or not, CLOSED (190).

Both, the training of the classifier and the application of the classifier, can be performed using the circuitry of a single pump. However, the training of the classifier may also be performed externally and the trained classifier may then be uploaded into the control system of the blood pump.

While in this embodiment only a single classifier was used, other embodiments may use more than one classifier, the further classifiers possibly being classifiers of different types, such as a support vector machine, a k-nearest neighbor operator or a neural network (feed-forward incl. hidden layers or nor e.g.). Furthermore, since the different classifiers have different strengths and weaknesses an approach employing several classifiers may increase the reliability of the classification. Additionally or optionally, the further classifiers may operate on a range of different signal characteristics. The combination of processing different signal characteristic by different classifiers may also increase the reliability of the classification in some embodiments.

FIG. 5 illustrates a schematic overview of a classification scheme 200.

In a first, optional step, the classification scheme receives a time-series signal of a flow rate between the right ventricle and the pulmonary artery. This signal is also preprocessed such that subsections of the signal include data from a heartbeat cycle only. From this data signal characteristics are derived in a step 210. These signal characteristics are fed to a trained classifier in a further step 220. The trained classifier labels the heartbeat cycle with a label of an open pulmonary valve or a closed pulmonary valve, i.e. into an open or closed state heartbeat cycle. It is noted that once a subsection of a time-series has been used to derive the valve state of said subsection, the data of the subseries is no longer necessary with respect to determining the valve state and in some examples may be discarded. However, in further examples the data may be stored in cases where the classifier can only classify the valve state of the heartbeat cycle by a small margin. This data subsection may later be used to improve the trained classifier, for example.

The inventors have found that, particularly in the pressure difference curve, a significant deviation is present between heartbeat cycles in which the aortic valve opens and in which the aortic valve remains closed.

The previous drawings helped to illustrate how different heartbeat cycles may be classified to represent an episode with an open or a closed valve. This classification may be used to control a blood pump system as will be illustrated with the help of FIGS. 6 through 8.

Figure 6:
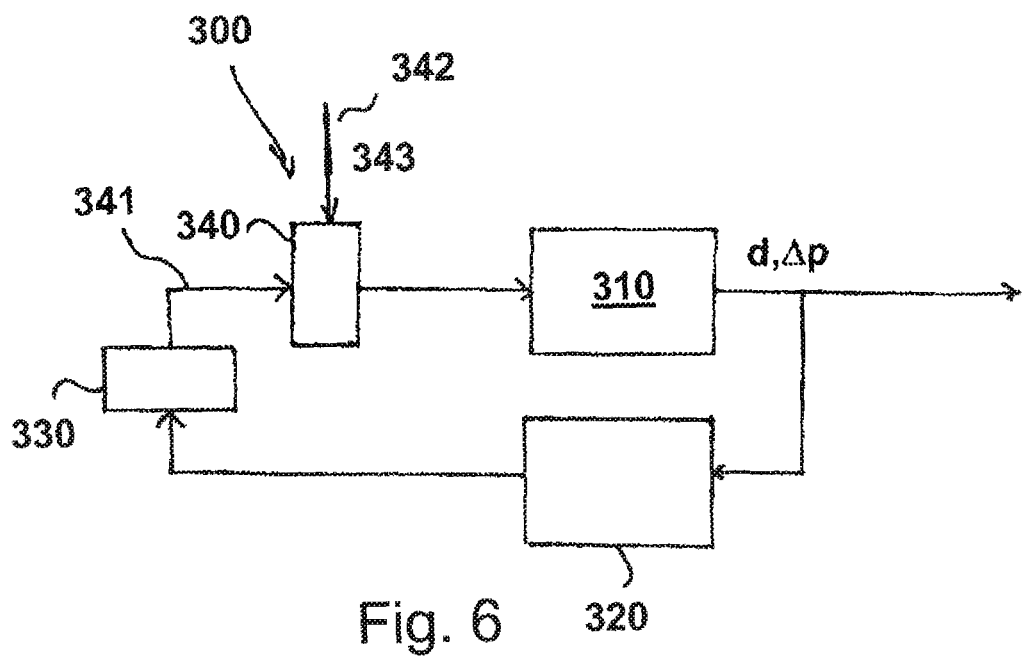
FIG. 6 illustrates a closed-loop control for a blood pump control system.

FIG. 6 illustrates a closed loop control system 300 of a blood pump system. The operational parameter to be controlled is the speed of the pump. Even though many different parameters may be operated, in the present embodiment, the pump is an axial flow pump with an outlet which is at a non-zero, preferentially 90°, angle to the axis of the axial flow pump. Examples of an embodiment of such a pump can be found in U.S. patent application Ser. Nos. 13/505,368, 14/115,425 or U.S. Ser. No. 14/115,460 which are incorporated herein in their entirety. More specifically, some embodiments include a rotor which, at least when rotating, is suspended between two hubs which border the rotor in an axial direction on both sides. However, the following control method may also be used with other types of axial flow pumps or turbo pumps, i.e. rotational or centrifugal pumps.

In the present embodiment the parameter to be controlled is the rotational speed n of an impeller of the pump. The measured output of this particular embodiment is the distance 310 of the rotating impeller from a hub. This distance is proportional to a pressure difference between an outlet of the blood pump and an inlet of the blood pump. In other words, while the measured variable in the present embodiment is not the pressure difference itself, a variable which is proportional to the pressure difference is measured. However, other embodiments may include measuring the pressure difference by employing a sensor in the area of the outlet of a blood pump and a further sensor in the area of the inlet of the blood pump. The pressure difference is translated into a time-series signal, which is divided into subsections representing time-series data of a heartbeat cycle only. These subsections are processed and a classifier 320 as described previously in this application is used to derive the valve state of the subsection.

The valve states and/or their occurrence in time are used to constructing an aortic valve opening index (AVOI) as an example of a valve state index (VSI). The AVOI 330 represents the percentage of heartbeat cycles with an open valve compared to all analyzed heartbeat cycles. The index has no dimension. In other embodiments, the index may be a closed valve index representing the percentage of heartbeat cycles with a closed valve state.

The AVOI 330 may be constructed in different ways. In some embodiments the AVOI may be based in the 10, 20 or 50 past heartbeat cycles. Additionally, several AVOIs may be constructed representing different time scales. While using more heartbeat cycles makes the index less prone to random events, using fewer cycles has the effect of more accurately describing the current state of a patient. The AVOI which is constructed from sensed data and which is used to control the pump will be referred to as AVOI or current AVOI. In contrast, a target AVOI is an AVOI value to which the current AVOI should adapt to due to a speed adaptation.

The mode of operation is controlled by an AVOI controller 340 and can be set externally. Different exemplary modes of operations are described in connection with FIG. 7, even though the subject matter is not limited to the modes described therein. The AVOI controller receives a current AVOI 341 from the AVOI constructing entity 330 and has been set externally to a mode of operation 342 which corresponds to a target AVOI 343. In the present example, the rotational speed of the pump is increased when the current AVOI is higher than the target AVOI and the speed of the pump is reduced when the current AVOI is smaller than the target AVOI. The adaption of the speed of the pump is controlled by controller 340. The controller may be a microprocessor, a programmable field-array, a microcontroller or software or firmware kept in a memory and processed by a processor such as described above. In a chosen example, the current AVOI is higher than the target AVOI and the speed of the pump is increased. The time it takes for an increase of speed to show in the current AVOI depends on the method of constructing the AVOI and the heart rate in some embodiments.

Figure 7:
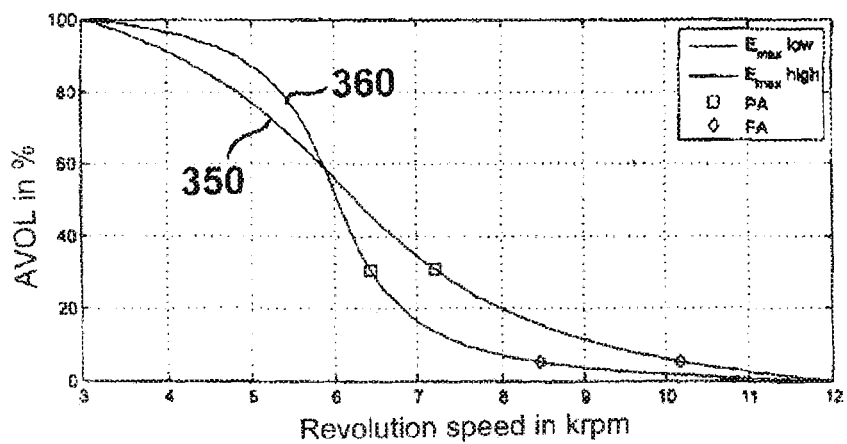
FIG. 7 illustrates an aortic valve opening index over the number of evolutions of a rotor as a moving member of a pump.

In this embodiment, the AVOI depends on the speed of the blood pump as is illustrated in FIG. 7. In the plot of FIG. 7, an AVOI in dependence on the number of rotations per minute, n, for a specific pump are shown. The dimension of n is kilo rounds per minute or krpm. The different curves shown in the plot refer to different values of the maximal value of the elasticity at the end of the systole, $E\_max$. The two curves 350 and 360 correspond to a smaller and a larger value of $E\_max$, respectively. It can be seen that the curve 350 corresponding to a small $E\_max$ value is flatter, while curve 360 corresponding to a larger $E\_max$ value has a more sigmoidal shape. In other words, different patients' hearts react differently to a change in the pump speed in that the change of the AVOI is different. However, each curve can be represented by a bijective function in that each value of n can be mapped to a different value of AVOI and vice versa.

The plot further shows a n-AVOI pair referring to a partial assist mode, PA, and a full assist mode, FA. These value pairs are of interest in some embodiments of the subject-matter of this application. The FA differs from the PA in that the aortic valve is permanently closed and only opens sporadically, if at all. In the plot of FIG. 7, the AVOIs are below 10%. The full assist mode offers a mode for allowing heart recovery without putting external stress on the heart since the pump is fully responsible for the pumping of blood. This is in contrast to the PA, which intends to let the heart do some, but not all of the pumping, so the heart can slowly recover to being able to pump the blood on its own. The FA mode may be further described by a maximal pump flow rate, a small LVEDV, a small LVSV, little movement of the myocardium, a small pulsatility of the aortic pressure, minimal external work and a minimal pressure-volume-area.

The PA mode of pump operation may be described by partially assisting the heart in its pumping operation. In particular, when the pump pumps between the left ventricle and the aorta, the aortic valve opens at least some of the heartbeat cycles, i.e. the AVOI is non-zero, but may be between 20% and 40%. For the chosen values of $E\_max$, the AVOI is PA mode is around 34%. Physiologically, this means that the ventricle still contributes to the pumping operation, which is indicated by the sporadic opening of the aortic valve. In different embodiments, the PA mode may be described by at least one of allowing a moderate pump flow rate (i.e. the pump does not contribute 100% to the flow rate between the ventricle and the aorta), a moderate left ventricular end-diastolic volume, LVEVD, a moderate left ventricular stroke volume, LVSV, a moderate movement of the myocardium, a moderate pulsatility of the aortic pressure, an increased external work by the heart itself, an increased pressure-volume area in a pressure-volume diagram. Furthermore, in the partial assist mode suction of the heart wall upon the inlet of the pump should not occur or only rarely occur.

For example, it is assumed that an implanted pump is operating within a patient whose heart has an E_max value comparable to the E_max value of curve 350. The pump includes a pump closed-loop control system as illustrated in FIG. 6. The current AVOI of the patient is 60% at about 6 krpm. The selected mode of operation is a PA mode, which corresponds to an AVOI in an interval between 30% and 35%. The interval can be made bigger or smaller in other embodiments, and as an effect of how fast the target AVOI can be reached and how often the speed needs to be adapted. A smaller interval usually requires a speed adaption more frequently than a bigger interval.

Figure 8:
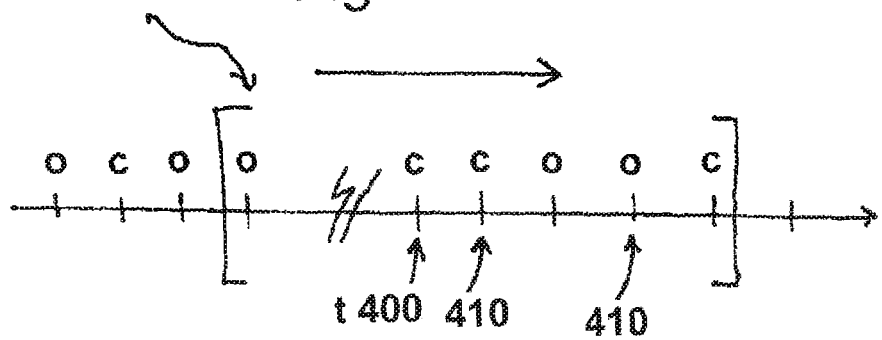
FIG. 8 illustrates an example of a sliding window approach for determining a current valve state index.

Different methods of updating an AVOI, or different VSIs, are explained in connection with FIG. 8. The shown embodiment illustrates a sliding window approach of updating the AVOI. The sliding window 400 has a width of 10, 20, 50 or more valve state indications 410. A valve state indication 410 denoted by "C" refers to a heartbeat cycle which was classified as a closed valve cycle and by "O" refers to a heartbeat cycle which was classified as an open valve cycle. If the different open or closed valve cycles are indexed by time, the times between different cycles may vary due to changes in the heart rate of the patient, for example. In the present example, the AVOI is constructed by using the, for example, past 50 valve state indications from the time of calculating the current AVOI. In other words, when a new valve state indication is generated, this valve state indication is used together with the preceding 49 valve state indications to derive the current AVOI. The valve state indication preceding the latest valve state indication by 50 indications is no longer used for constructing the AVOI and may be deleted from a memory in which the values used for the AVOI construction are stored. This memory may be volatile or non-volatile and can be part of a main memory of the pump control system, for example. A different embodiment of constructing the AVOI is to reconstruct the AVOI every, for example, 30 valve state indications using these 30 valve state indications only. In further embodiments, the AVOI construction may also include the preceding 30 valve state indications. Instead of counting the number of occurred valve state indications, the AVOI may also be reconstructed after a predetermined interval of time, such as 30, 45, or 60 seconds, regardless how many valve state indications have been generated in this interval. In further embodiments, the number of open or closed valve indications may be counted and the AVOI may be reconstructed after this preset number of open or closed valve state indications. Furthermore, in other embodiments, the AVOI may be constructed by using a sliding window approach, however, instead of reconstructing the AVOI after each new valve state indication, the AVOI is reconstructed after each $10^{th}$, $20^{th}$ or $30^{th}$ new valve state indication.

Figure 9:
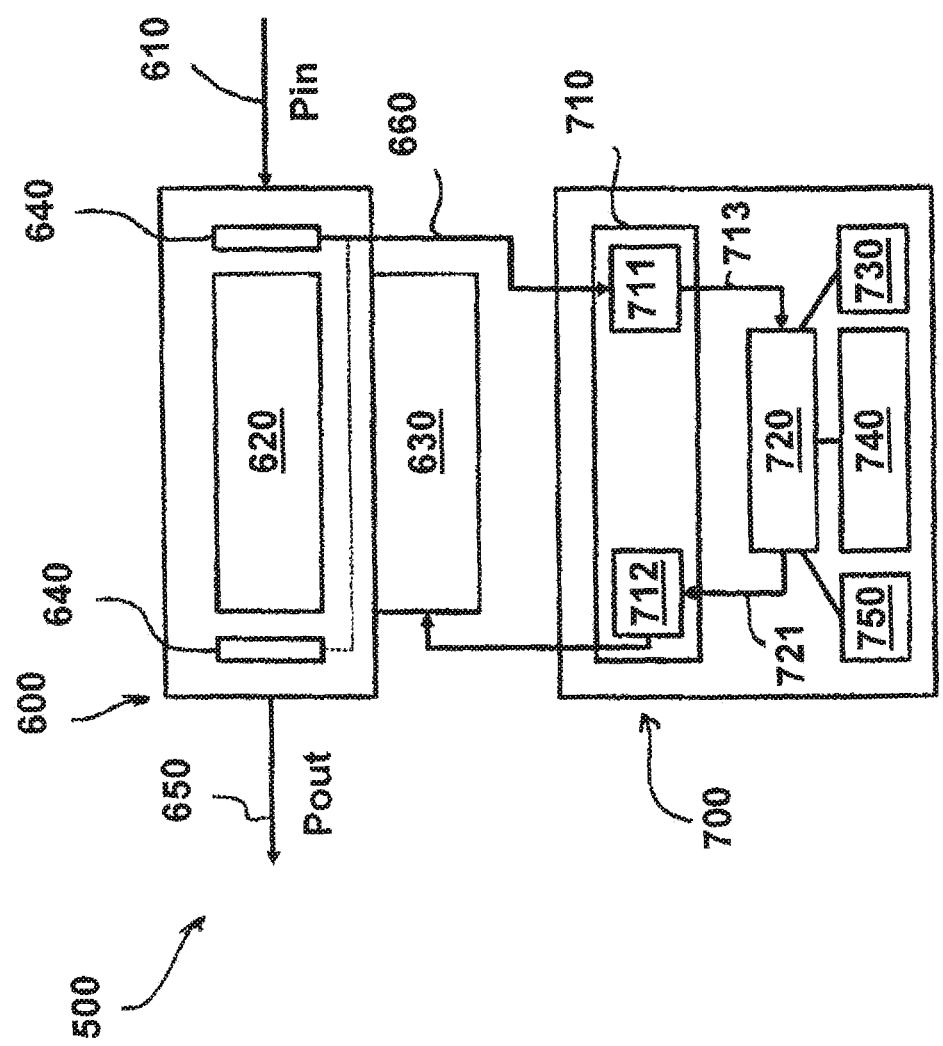
FIG. 9 shows an example of a blood pump and a blood pump control system.

An embodiment of a blood pump control system is illustrated in FIG. 9. The system 500 includes an implantable blood pump 600 and a control unit 700. The control unit may be configured for implantation or may be configured for controlling the pump operation from outside of the body.

The blood pump and the control unit may be connected by means of cables or wires or by means of a wireless data connection. The system may also include a transcutaneous energy transfer system to deliver energy to the blood pump too be used for rotating the rotor.

The blood pump 600 includes an inlet 610, which may be connected to the left or right ventricle or an atrium or a pulmonary vein either directly or via means of a canula. Blood entering the inlet 610 has a pressure p_in, which may be measured directly by a sensor located in the inlet. The blood is pumped by means of a rotor 620 driven by a brushless DC motor, BLDC, 630 and its axial position being controlled actively by a sensing coil or a plurality of sensing coils located in the stator hubs 640. Permanent magnets located in the rotor and the stator hubs allow for a passive radial control of the position of the rotor. Blood exits the pump through a blood outlet 650 at a pressure of p_out, which may be measured directly by means of a sensor located in the area of the outlet of the pump. However in the present embodiment, the inlet pressure and the outlet pressure are not measured directly. Instead the axial distance between the rotor and the stator hub can be sensed by the sensing coils. Optionally, in combination with an axial force delivered by a ring coil the distance can be delivered to a lookup-table, for example, and it has been found that this distance is almost linearly proportional with a pressure difference over the rotor. Thus, the distance can be used as a signal representative of a pressure difference between the pump outlet and inlet without having to measure the pressure or pressure difference directly. In other embodiments or for other pumps the measured signal may be the pressure or pressure difference directly or from another signal source than the distance.

The signal representing the distance between the stator hub and the rotor is forwarded to the control unit 700 as an analogue or digital signal and is transmitted via cable or wirelessly.

In this embodiment, the signal 660 is received at a signal pre- and post-processing circuit 710 of control unit 700. The signal pre-processing circuit 711 may improve the signal-to-noise ratio of the signal, or may include a digitizing step, or may include the application of a frequency filter. Furthermore, the circuit may be configured to divide the signal into subsections containing data from a single heartbeat cycle only. The circuit may be a hard-wired circuit, a microcontroller, a programmable field array or may be simulated in a microprocessor by means of a software or firmware stored in a memory. The circuit may be an analogue or a digital circuit.

The pre-processed signal 713 is forwarded to a microprocessor 720, which is connected to a signal-processing circuit 730, a memory 740 and a mode operation setting unit 750.

The signal-processing circuit 730 may be a hard-wired circuit or an emulated software circuit and routine processed by the microprocessor 720. The pre-processed signal 713 is a time-series signal and signal characteristics are extracted from the signal and stored as a signal characteristics vector for the heartbeat cycle. In further example, in which the signal includes more than one heartbeat cycle the extracted signal characteristics may also be stored in a matrix, a column or row for each heartbeat cycle. The extracted vector is processed by a classifying circuit and reduced to a valve state indication for each vector as previously indicated. The valve state indication is then used to construct an AVOI.

Valve state indications used for constructing the AVOI may be temporarily stored in a part of the memory 740. This part of the memory can also be realized as a ring buffer, or any other type of volatile or non-volatile memory. The constructed AVOI is compared to a target AVOI corresponding to a mode of operation set in the mode unit 750. The comparison may take place in the microprocessor 720 or may be performed by a comparator circuit. Depending on the result of the comparison, the microprocessor generates a signal 721 indicative of a desired rotational speed of the pump. The signal may reduce, increase or maintain the current rotational speed. The signal 721 is post-processed, if necessary, and forwarded by transmitter 712 of the pre- and post-processing circuit 710 to motor 630. The motor speed is altered according to the signal.

In further embodiments, the AVOI can be stored in regular intervals and transmitted to an external programmer. Based on the AVOIs, the programmer can change the mode of operation from one mode to another or can change the target AVOI range set for a specific mode or can upload new modes of operation.

Figure 10A:
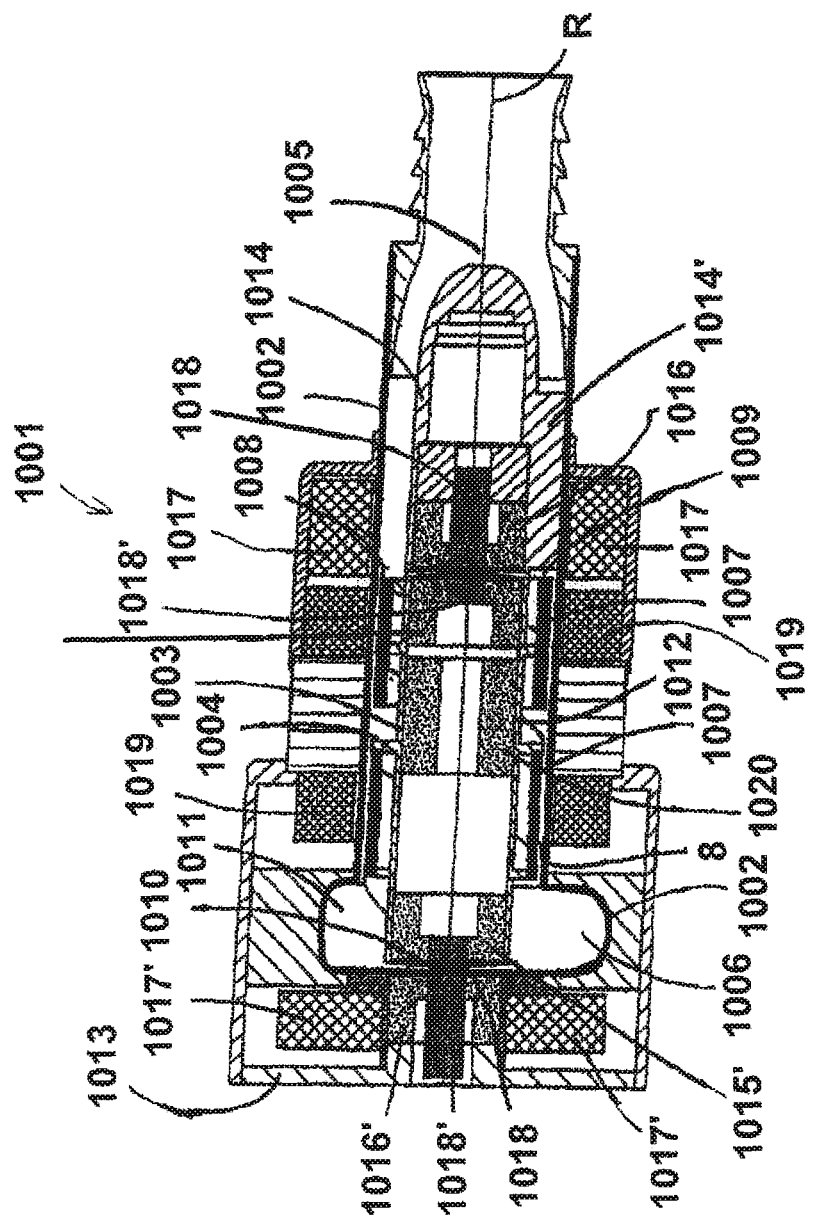
FIGS. 10a, b more detailed embodiments of blood pumps.
Figure 10B:
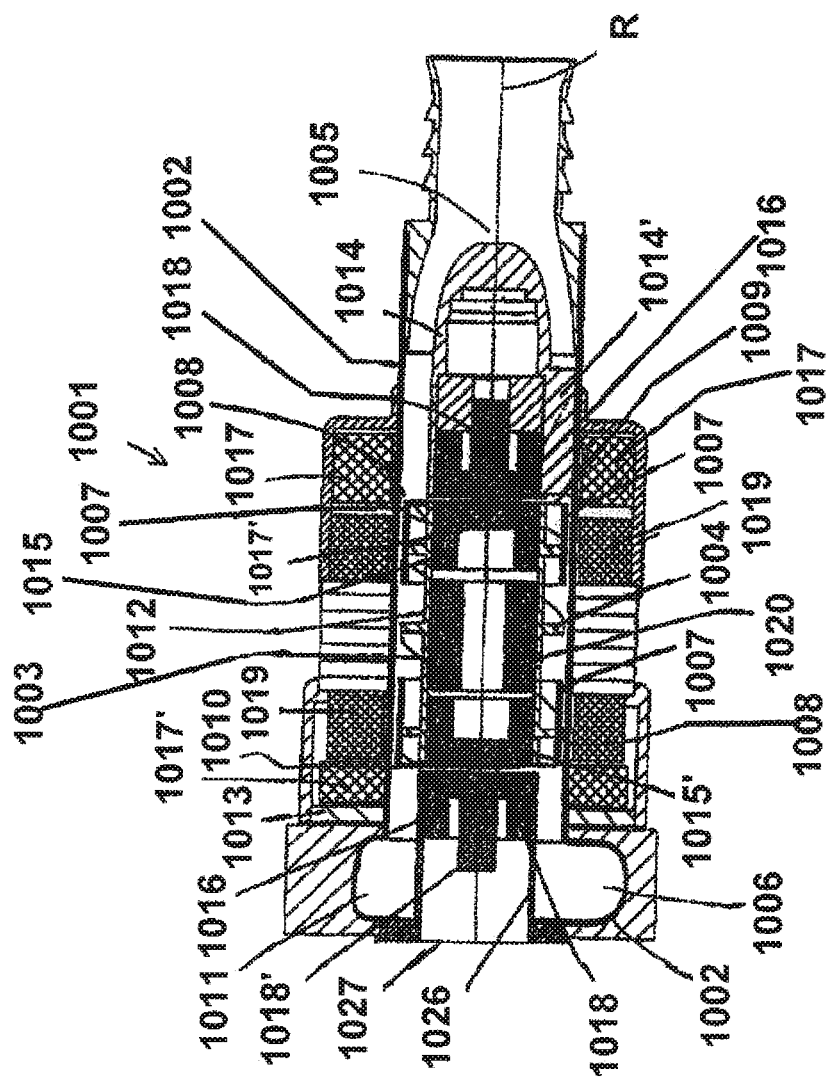

A schematic representation of a longitudinal section through a blood pump 1 of the type suggested here is represented schematically in FIG. 10b. The blood pump 1001 comprises a hollow body 1002 (represented as a continuous thick line), in which an impeller 1003 with a blading 1004 is provided. Moreover, the hollow body 1002 comprises an inlet 1005 for the flow of blood in an inflow direction which is parallel to a rotation axis R (shown dashed), and an outlet 1006 for the outflow of blood in an outflow direction which runs perpendicular to the section plane. Accordingly, in this embodiment example, the outlet is arranged offset at a right angle relative to the rotation axis R, for producing an outflow angle α of α=90°, which is different from zero, between the inflow direction and the outflow direction. However, the angle α may also differ from 90°.

The outlet 1006 of the hollow body 1002 is arranged between an upstream-side 1009 of the impeller 1003, said upstream-side facing the inlet, and a downstream-side 1010 of the impeller 1003, said downstream-side being away from the inlet. An inner radius of the hollow body 1002 serves for forming a discharge channel 1011 which runs tangentially around the impeller 1003 and runs out into the outlet 1006, for a discharge of the blood out of the hollow body 1002, said discharge running essentially tangentially to the impeller 1003.

Moreover, two support rings 1007 are connected to the impeller 1003, for the formation of two annular gaps 1008 between the support rings 1007 and an inner wall of the hollow body 1002.

A peripheral surface 1012 of the impeller 1003, which carries the blading 1004, is formed in a cylinder-shaped manner, but may just as well be designed in a truncated-cone-shaped or cone-shaped manner. The axial dimension (length) L of the impeller is selected larger than a diameter D of the impeller on the downstream-side of the impeller. The blading of the impeller is characterised by a pitch which increases towards the outlet 1006. In this manner one permits an axial propulsion up to the discharge channel 1011, which is particularly gentle to the blood. The blading of the impeller 1004 extends axially completely (in other embodiments partly or not at all) into the discharge channel 1011 and the outflow 1006.

An inlet guide vane 1014 which is provided with a blading 1014', is provided in the direct vicinity of the upstream-side 1009 of the impeller 1003.

The blood pump further comprises a partly actively stabilised bearing device which contains an actively stabilised, magnetic axial bearing as well as a passive, magnetic radial bearing. The magnetic bearing device firstly comprises two permanent magnets 1015, 1015' which are arranged in the impeller at the upstream-side and at the downstream-side. Furthermore, two further permanent magnet bearings 1016, 1016' which are poled opposite to these (attracting) and which are integrated into the inlet guide vane 1014 and the backing plate 1013, respectively, serve the formation of the passive, magnetic radial bearing, which ensures that the impeller 1003 is held in a radial desired position between the inlet guide vane 1014 and the backing plate 1013. Moreover, for the actively stabilised magnetic axial bearing, two ring coils 1017, 1017' are arranged outside the hollow body 1002, in front of and behind the impeller 1003, such that they are peripheral around the hollow body 1002 in an annular manner for producing an axial magnetic flux. Moreover, the magnetic bearing device comprises a sensor system which comprises distance sensors 1018, 1018' integrated into the inlet guide vane 1014 and/or the backing plate 1013 as well as into the impeller 1003, for measuring the gap widths between the impeller 1003 and the inlet guide vane 1014 or the backing plate 1013, as well as a closed-loop control unit (not shown here) which is connected to the distance sensors 1018, 1018' and the ring magnets, said closed-loop control unit setting the magnet flux produced by the ring magnets, according to the measured axial position of the impeller, for correcting a possible deviation of the impeller from an axial desired position.

Finally, a motor winding 1019 running around the hollow body and a motor magnet 1020 integrated into the impeller are provided, said motor magnet being magnetised in an alternating radial manner, for driving the impeller 1002.

In FIG. 10b, a schematic representation of a longitudinal section through a blood pump 1001 of the type suggested here is shown, which differs from the blood pump described by way of FIG. 10a in that a central, cylindrical rod 1016 extends from a downstream-side 1027 of the pump 1001 axially into the hollow body 1002 towards the impeller 1003. In said rod 1026, one of the distance sensors 1018' is integrated for measuring the gap width between the impeller 1003 and the rod 1026 as well as one of the permanent magnet bearings 1016' being a part of the passive, magnetic radial bearing. Furthermore, the ring coil 1017' of the actively stabilized axial bearing now is positioned axially before the outlet 1006 and runs around the hollow body 1002, while in the embodiment shown in FIG. 10a, the respective ring coil 1017' is located behind the hollow body 1002 (with respect to the axial pump direction) and consequently does not run around the hollow body 1002.

Both pumps shown in FIGS. 10a and 10b may incorporate any of the methods or systems described in this application. Further details of the pumps can be found in applications PCT/EP2011/002384, US application Ser. No. 13/505,368 and PCT/EP2012/002009, which are incorporated herein by reference.

The invention claimed is:

1. An electronic circuitry of a blood pump control system for controlling a blood pump configured to, and/or a non-transitory computer readable medium comprising computer-executable instructions executable to, perform a method comprising:

measuring a plurality of heartbeat time-series signals by one or more sensors located in or adjacent to the blood pump and/or disposed in an area of at least one of an outlet and an inlet of the blood pump configured to detect a pressure difference and/or a signal proportional to the pressure difference;

deriving a first data set of a signal characteristic from a first group of the heartbeat time-series signals, the first group representing heartbeat cycle data when a valve state of a valve was open during a heartbeat cycle, the first group of the heartbeat time-series signals indicative of a pressure difference between a first pressure representative of a ventricular pressure and a second pressure representative of an aortic pressure;

deriving a second data set of the signal characteristic from a second group of the heartbeat cycle time-series signals, the second group representing heartbeat cycle data when a valve state of a valve was closed during the heartbeat cycle, the second group of the heartbeat time-series signals indicative of the pressure difference between the first pressure representative of the ventricular pressure and the second pressure representative of the aortic pressure;

training a classifier data structure to discriminate at least the open and closed valve states based on the first data set and the second data set; and controlling the blood pump based on an output of the classifier data structure after the classifier data structure has been trained.

2. The electronic circuitry and/or the non-transitory computer readable medium of claim 1, wherein the classifier data structure is a neural network, support vector machine, Gaussian, Naïve Bayes, decision tree, linear discriminant analysis or a k-nearest neighbour classifier.

3. The electronic circuitry and/or the non-transitory computer readable medium of claim 1, wherein the classifier data structure is used for classifying in a method for generating a signal indicative of a valve state of a heart valve, the method for generating the signal comprising:

receiving a time-series signal from a third group of heartbeat cycle time-series signals representing a pressure difference between a first blood pressure and a second blood pressure over at least one heartbeat cycle;

deriving the signal characteristic from the time-series signal received from the third group of heartbeat cycle time-series signals;

classifying the valve state of the heart valve during the at least one heartbeat cycle based on the signal characteristic; and generating the signal indicative of the valve state based on the classification.

4. The electronic circuitry and/or the non-transitory computer readable medium of claim 1, wherein the signals of the first and the second group are recorded while simultaneously using ultrasound imaging to determine whether the valve state was open or not.

5. The electronic circuitry and/or the non-transitory computer readable medium of claim 1, wherein the signals of the first and the second group are recorded while simultaneously recording a plurality of heart sounds.

6. The electronic circuitry and/or the non-transitory computer readable medium of claim 5, wherein the heart sounds are recorded by an acoustic transducer.

7. The electronic circuitry and/or the non-transitory computer readable medium of claim 1, wherein a second signal is included in any of the first group of the heartbeat time-series signals or the second group of the heartbeat time-series signals, wherein the signal characteristic of the second signal includes at least one of:

a difference between a minimal and a maximal signal value of the second signal during a heartbeat cycle;

an extremal value of a derivative of the second signal between a minimal and a maximal signal value of the second signal during a heartbeat cycle;

a quotient of a difference between a minimal and a maximal signal value of the second signal during a heartbeat cycle and a maximal signal value of the second signal within a predetermined number of previous heartbeat cycles;

a difference between an end value defined by an intersection value of a first tangent line of the second signal through an extremal point of the second signal and a second tangent line through a minimal signal value;

an area bordered by the first and second tangent lines; and an angle between the first tangent line through the extremal point of the second signal and a line connecting the minimal signal value of the second signal and a value of the second signal corresponding to an end value ($\alpha$).

8. The electronic circuitry and/or the non-transitory computer readable medium of claim 1, wherein any of the first group of the heartbeat time-series signals or the second group of the heartbeat time-series signals is reduced to a vector representing the signal characteristic or a higher-order signal characteristic.

9. The electronic circuitry and/or the non-transitory computer readable medium of claim 8, wherein the vector includes opening and closing times of the valve.

10. The electronic circuitry and/or the non-transitory computer readable medium of claim 8, wherein the vector includes timing information.

11. The electronic circuitry and/or the non-transitory computer readable medium of claim 1, wherein the classifier data structure includes more than one classifier.

12. The electronic circuitry and/or the non-transitory computer readable medium of claim 1, wherein the classifier data structure is trained until it has a predetermined confidence interval of at least one of specificity, sensitivity or reliability.

13. An electronic circuitry configured to, and/or a non-transitory computer readable medium comprising computer-executable instructions executable to, perform a method comprising:

measuring a plurality of heartbeat time-series signals by one or more sensors configured to detect a pressure difference and/or a signal proportional to the pressure difference, the one or more sensors located in or adjacent to a blood pump and/or disposed in an area of at least one of an outlet and an inlet of the blood pump;

deriving a first data set of a signal characteristic from a first group of the heartbeat time-series signals, the first group representing heartbeat cycle data when a valve state of a valve was open during a heartbeat cycle, the first group of the heartbeat time-series signals indicative of a pressure difference between a first pressure representative of a ventricular pressure and a second pressure representative of an aortic pressure;

deriving a second data set of the signal characteristic from a second group of the heartbeat cycle time-series signals, the second group representing heartbeat cycle data when a valve state of a valve was closed during the heartbeat cycle, the second group of the heartbeat time-series signals indicative of the pressure difference between the first pressure representative of the ventricular pressure and the second pressure representative of the aortic pressure;

training a classifier data structure to discriminate at least the open and closed valve states based on the first data set and the second data set, the classifier data structure comprising a probabilistic classifier; and controlling the blood pump based on an output of the classifier data structure after the classifier data structure has been trained.

14. The electronic circuitry and/or the non-transitory computer readable medium of claim 13, wherein the probabilistic classifier includes a neural network.

15. The electronic circuitry and/or the non-transitory computer readable medium of claim 13, wherein the method further comprises applying a signal indicative of a valve state of a heart valve to the classifier data structure to generate a signal indicative of a valve state of the heart valve.

16. The electronic circuitry and/or the non-transitory computer readable medium of claim 13, wherein the one or more sensors is and/or are configured to detect an axial displacement of a rotating member of a blood pump as the signal proportional to the pressure difference, and/or wherein the one or more sensors includes a bearing of the blood pump and/or a measurement coil of an axial bearing.

* * * * *